(12) United States Patent
Pero et al.

(10) Patent No.: US 6,773,702 B2
(45) Date of Patent: Aug. 10, 2004

(54) USE OF COMBRETASTATIN A4 AND ITS PRODRUGS AS AN IMMUNE ENHANCING THERAPY

(75) Inventors: Ronald W. Pero, Sandgate, VT (US); Francis Y. F. Lee, Yardley, PA (US); Klaus Edvardsen, Lund (SE); Hans Olov Sjögren, Lund (SE)

(73) Assignees: OXiGENE, Inc., Waltham, MA (US); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/034,746

(22) Filed: Dec. 26, 2001

(65) Prior Publication Data

US 2002/0160973 A1 Oct. 31, 2002

Related U.S. Application Data

(60) Provisional application No. 60/258,283, filed on Dec. 26, 2000.

(51) Int. Cl.$^7$ .................. A61K 48/00; A61K 33/00; A61K 33/42; A61K 38/19
(52) U.S. Cl. ................ 424/93.21; 424/93.1; 424/93.2; 424/600; 424/601; 424/185.1; 435/320.1; 514/731; 514/733; 514/464; 514/720; 514/721
(58) Field of Search ............... 435/320.1; 424/93.1, 424/93.2, 93.21, 600, 601, 185.1, 93.6; 514/731, 733, 464, 720, 721

(56) References Cited

U.S. PATENT DOCUMENTS

| | | | |
|---|---|---|---|
| 4,996,237 A | 2/1991 | Pettit et al. | |
| 5,409,953 A | 4/1995 | Pettit et al. | |
| 5,561,122 A | 10/1996 | Pettit | |
| 5,561,953 A | 10/1996 | Rotter | |

FOREIGN PATENT DOCUMENTS

| | | |
|---|---|---|
| WO | WO 99/35150 | 7/1999 |
| WO | WO 00/48606 | 8/2000 |

OTHER PUBLICATIONS

Gura, T., Science, 1997, vol. 278, pp. 1041–1042.*
Gomez–Navarro et al., European Journal of Cancer, 1999, vol. 35, No. 6, pp. 867–885.*
Dark, et al. (1997). *Cancer Research* 57: 1829–1834.
Tozer, et al. (1999). *Cancer Research* 59: 1626–1634.
Chaplin, et al. (1996). *Br. J. Cancer* 74(suppl 27):S86–S88.
Iyer, et al. (1998). *Cancer Research* 58: 4510–4514.
Springer, et al. (2000). *Mol. Ther.* 1(1):82–87.
Hegardt, et al. (2001). *Cancer Immunol Immunother* 50: 491–501.
Hegardt, et al. (2001). *Cell Immunol* 200: 116.
Green, et al. (1982). *Anal Biochem* 126:131.
International Search Report for PCT US 01/49622, mailed Aug. 20, 2002.
Siim, et al. (2000). *Cancer Research* 60:4582–4588.
Parkins, et al. (2000). *Br. J. Cancer* 83(6): 811–816.
G.G. Dark et al., "Combretastatin A–4, an Agent that Displays Potent and Selective Toxicity toward Tumor Vasculature," Cancer Res., 57:1829–1834 (1997).
U.S. patent application Ser. No. 09/505,402, Pero et al., filed Feb. 16, 2000.

* cited by examiner

*Primary Examiner*—David Guzo
(74) *Attorney, Agent, or Firm*—Ivor R. Elrifi, Esq.; Naomi S. Biswas, Esq.; Mintz, Levin, Cohn, Ferris, Glovsky and Popeo, P.C.

(57) ABSTRACT

A method of treating immune suppression in a warm-blooded animal bearing a tumor, by administering to the animal an amount of combretastatin A4 and/or a prodrug thereof effective to enhance immune responsiveness without causing vascular destruction. Immunotherapy treatment to inhibit or kill tumor cells includes administering to the animal an immune-response-stimulating agent such as a vaccine of tumor cells genetically modified to produce an immune-response-enhancing cytokine while counteracting tumor-induced immune suppression in the animal by administering combretastatin A4 and/or a prodrug thereof.

13 Claims, 7 Drawing Sheets

USE OF COMBRETASTATIN A4 AND ITS PRODRUGS AS AN IMMUNE ENHANCING THERAPY

CROSS REFERENCE TO RELATED APPLICATION

This application claims the priority benefit under 35 U.S.C. §119(e) of U.S. provisional patent application No. 60/258,283 filed Dec. 26, 2000, the entire disclosure of which is incorporated herein by this reference.

FIELD OF THE INVENTION

This invention relates to new methods for treating tumor bearing animals including humans with a sufficient amount of Combretastatin A4 or its prodrugs to permit tumor regression but at doses that do not cause vascular shut-down.

BACKGROUND OF THE INVENTION

Cancer is a serious and pervasive disease worldwide. The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Although cancer is commonly considered to be a single disease, it actually comprises a family of diseases wherein normal cell differentiation is modified so that it becomes abnormal and uncontrolled. As a result, these malignant cells rapidly proliferate. Eventually, the cells spread or metastasize from their origin and colonize other organs, eventually killing their host.

In addition to alterations in cell growth regulation, cellular transformation during the development of malignant cancer involves multiple alterations in the normal pattern of cell morphology. Cancer cells are morphologically restructured to enhance their invasive properties. The accumulation of genetic modifications (mutation, gene amplification, chromosomal deletion or translocation) may lead to the expression of aberrant molecules or the altered expression of normal molecules. When these genetic modifications are manifested as alterations in the cell-to-cell associations within a tissue of origin, a malignant and metastatic cancer may develop. In the process of metastasizing, they may invade adjoining tissue before spreading to distant sites through the circulatory system. The metastatic cells can adhere to endothelial cells to aid their migration, but ultimately they escape from the circulation and begin growth in a foreign environment.

To invade a distant site, metastatic cells often produce elevated levels of both receptors for the basal lamina proteins and enzymes that digest collagen and other extracellular proteins, such as proteoglycans and glycosaminoglycans. As these proteins are disentegrated, the tumor cells penetrate the lamina and invade the foreign tissue. Once they have invaded a foreign tissue, tumor cells must be able to adhere to new types of cells and proliferate without a mass of surrounding identical cells. Therefore, the wide range of altered behaviors that underlie metastasis may have their basis in a new or variant surface protein made by the metastatic tumor cell.

Tumor Immune Surveillance

It might be expected that gross cell-surface alterations associated with malignancy would lead the immune system to recognize tumor cells as foreign. Indeed, there are a number of immune surveillance mechanisms by which abnormal cells are recognized early in the development of a tumor and destroyed. This antitumor effect can be demonstrated with a tumor transplantation test involving isograft rejection. When a tumor is grafted onto an animal previously immunized with inactivated cells of the same tumor, resistance to the graft is observed. This is because the tumor host is able to mount an immune reaction against tumor-specific transplantation antigens (TSTAs) on the surface of the tumor cells. Molecular cloning techniques have been used to identify TSTAs as mutant homologs containing slight variations from the sequence of a normal gene. In other instances, the TSTA gene is identical to the parental gene, but its expression is altered.

Histological studies of human tumors have shown that some contain a marked infiltrate of inflammatory immune cells, including lymphocytes, macrophages, dendritic cells, and granulocytes. Some of these cells can suppress tumor growth or metastasis by mounting a humoral immune response and producing antibodies against a tumor antigen. Some of these antibodies may interfere with tumor growth directly or they may mediate a tumor immune response by activating antibody-dependent cell-mediated toxicity (ADCC) or the complement system. While these mechanisms are important, an immune response generating cytotoxic effector cells is often much more effective. This type of immune response serves to lyse target cancer cells and, when sufficiently strong, results in tumor elimination.

There are three main types of cytotoxic effector cells that are capable of recognizing and destroying tumor cells:

1) Cytotoxic T lymphocytes (CTL). Activation of CTL can occur by recognition of tumor antigen on the MHC class I either of an antigen presenting cell (e.g. a dendritic cell or a macrophage) that has engulfed tumor cell fragments and which are also providing necessary costimulatory signals, e.g. by the B7 molecule, or alternatively of a tumor cell provided that T-cell produced cytokines are present to give costimulation. When activated, these cells kill tumors in an antigen-specific and MHC class I-restricted manner by releasing an arsenal of cytotoxic compounds including perforin, granzymes, IFN-γ, and TNF-α.

2) Macrophage cells. These cells are primarily activated by the IFN-gamma and kill tumor cells in a nonspecific, MHC-unrestricted fashion by the same mechanisms they use to kill microorganisms (TNF-α, lysozyme, reactive oxygen intermediates, nitric oxide).

3) Natural Killer (NK) cells. NK cells kill tumor cells in an MHC-unrestricted way by recognizing various membrane molecules including adherence molecules in the absence of inhibitory signals provided by membrane MHC class I of tumor cells. Effector mechanisms include perforin, granzymes, IFN-γ, and Fas-L mediated apoptosis.

Tumor Escape Mechanisms

Despite the elaborate defense mechanisms of the host immune system, tumor cells find ways to elude immune detection and kill the host. A variety of mechanisms have been proposed to explain evasion:

1) Lack of co-stimulatory molecules—Many tumors are only weakly immunogenic. This is not necessarily because the antigens are lacking, but because the antigens are presented without the necessary costimulation. Activation of CTL requires co-stimuli, which may be cell-surface molecules or cytokines secreted by APCs or T cells. The B7 molecule, present on specialized APCs, is now known to be a key co-stimulus acting via its counter-receptor CD28 on the T-cell surface. Interaction of T cells with tumors that lack the co-stimulatory B7 molecule renders the T cells anergic and unable to respond to the tumor if alternative costimulation is not provided by T cell produced cytokines.

Equally important is that tumors may also show a reduction or a complete loss of MHC Class I molecules on their cell surface.

These antigens are required for the presentation of tumor antigen peptides, and in their absence a cytotoxic T cell is incapable of even binding the tumor cell. Furthermore, some tumor cells may lack receptor molecules required for lymphocyte adhesion (e.g., LFA-1 or ICAM-1) or they may express anti-adhesive molecules (e.g., Mucin).

2) Blocking antibodies—Many tumors are capable of shedding tumor antigens. Complexes composed of antibodies and shed tumor antigens can saturate the Fc receptors on effector cells, preventing them from interacting with tumor cells.

3) Antigenic Modulation—Binding of a TSTA by antibody can induce internalization of the antigen by endocytosis. Degradation of the antigen eliminates a potential target of cell-mediated immune response.

4) Secretion of Immunosuppressive Factors—Tumors can secrete immunosuppressive cytokines such as Transforming Growth Factor (TGF-$\beta$), Prostaglandin E2 (PGE2), or IL-10. These factors inhibit the development and proliferation of cytolytic T cells.

Cancer Immunotherapy

Due to the wide variety of cancers presently observed, numerous strategies have been developed to destroy cancer within the body. Currently the top three methods of treating cancer in the United States include surgery, chemotherapy, and radiation therapy. While these treatments have been successful for many patients, they suffer a number of problems including toxicity, non-selectivity, relapse of cancer, and immunosuppression. For instance, before leukemia patients receive bone marrow transplants, they receive massive doses of chemotherapy and radiation to destroy all leukemia cells. This leaves the individuals immunosuppressed and vulnerable to infections, such as cytomegalovirus infection (CMV).

Researchers have long sought to exploit the disease-fighting abilities of the immune system for the purpose of fighting cancer, especially for second-line therapy or for patients in which conventional therapy is not an option. These types of treatments can be classified as active or passive, specific or non-specific.

1) Passive-nonspecific immunotherapy—The efficiency of systemic administration of cytokines such as IFN-$\alpha$, IFN-$\gamma$, IL-2 or TNF-$\alpha$ is limited.

2) Passive-specific immunotherapy—Antibody-based therapies in which a tumor antigen is targeted by monoclonal antibody, either alone or coupled to a drug, a pro-drug, toxin, cytokine, or radioisotope. Although this treatment has experienced some successes, limitations include a low bioavailability in large tumor masses, lack of circulation to diffuse tumor sites, and nontarget cell binding causing dose-limiting side effects. Similarly, transfer of T cells obtained from the patient's own tumor tissue, from which they may be isolated and grown to large cell numbers in vitro in the presence of the growth factor IL-1, has been shown to inhibit tumor growth in some cases.

3) Active-nonspecific immunotherapy—A variety of agents have been used for non-specific stimulation of the immune system. The strategy employs a strongly immunogenic vaccine to act as a general boost to immune response. Exactly which immune system component accounts for the killing remains unknown and the results are highly unpredictable. Even so, the tactic has had some real success. For example, use of the tuberculosis BCG vaccine has been effective against recurrent bladder cancer.

4) Active-specific immunotherapy—Use of an inactivated tumor cell "vaccine" has been investigated for many years as a means of making tumor antigens more immunogenic. Immunomodulatory gene therapy, a procedure whereby a host is vaccinated with its own tumor cells, has recently received much interest. The tumor cells in this case are transfected with DNA for the co-stimulator B7 gene or an immunopotentiating cytokine (IL-2, IL-4, IL-12, IL-18, IFN-$\gamma$, or granulocyte-macrophage colony stimulating factor (GM-CSF)). The tumor cell vaccine serves to activate preferentially proliferation of anti-tumor cytototoxic T cells.

Tumor-Induced Macrophage Immunosuppression

Immunomodulatory gene therapy is potentially an ideal treatment in that it can be customized to an individual cancer patient in order to provide a long-lasting cure. While this method can protect animals when administered prior to tumor challenge, attempts to induce regression of established tumors have been much less successful. Recent evidence suggests that a novel tumor-induced immunosuppressive mechanism may be responsible for the ineffectiveness of the treatment in tumor-bearing animals. Despite the effective activation of cytotoxic T cells by coexpression of tumor antigen and co-stimulant, the effector response itself is dampened. Several reports have demonstrated that the impaired responsiveness of T cells may be due to the effects of tumor-associated macrophages. As part of their cytotoxic effector function, macrophages are capable of producing reactive oxygen intermediates (ROIs) and Nitric Oxide (NO), molecules which are highly toxic to tumor cells. In tumor-bearing animals however, an enhanced production of NO has immunosuppressive effects on T-cell function. These effects include induction of T-cell apoptosis, suppression of cytokine production, inhibition of T-cell proliferation, and suppression of the cytolytic response.

NO is produced by macrophages through the action of the cytokine-inducible isoform of Nitric Oxide Synthase (iNOS) NOS combines oxygen with arginine in the presence of a cofactor to produce NO. Although macrophages of normal tumor-free animals and patients express iNOS and have a basic reasonably high production of NO, macrophages of tumor bearers have been shown to have an enhanced expression of this enzyme, which results in a significant overproduction of NO and more or less pronounced immunosuppressive effects. In addition, iNOS is optimally activated by many of the same cytokines used in immuno-gene therapy. While IL12, IL-18, and IFN-$\gamma$ are all powerful inducers of a cytotoxic response, they are also strong activators of NO production. Therefore, in order for immuno-gene therapy to be successful it has been recognized that a means of reducing NO production is required. For example, inhibition of NOS function in the macrophage population would enable tumor-bearer lymphocytes to escape tumor-induced immunosuppression and become reactive to cytokine-producing tumor cells. The effects of L-NAME, a competitive NOS inhibitor, have been tested on isolated macrophages from tumor-bearing animals. These experiments demonstrated that tumor-induced immunosuppression effects could be mostly eliminated when the NO production is reduced to the level of that produced by macrophages from tumor-free animals.

Although the use of NOS inhibitors has resulted in significant enhancement of an anti-tumor response in tumor-bearing animals, the dose required for this effect (0.5 mg/ml) is highly toxic and prohibits its use in a clinical setting. In addition, although iNOS selective inhibitors do exist, many NOS inhibitors are broad spectrum and are able to alter the activity of the alternate endothelial NOS (eNOS) and neural NOS (nNOS) isoforms. The potential for side effects is great. There is therefore an urgent need for NO-reducing agents that can be used in combination with immunotherapy in a therapeutic capacity. Such an agent would eliminate the tumor-induced immunosuppression that tends to develop and increase the likelihood that immunogene therapy involving increased levels of IFN-γ, IL-12 or IL-18 will be adopted as a viable alternative to traditional cancer treatments.

Combretastatin A4 and its Prodrugs

The combretastatins are a group of naturally occurring cytotoxic agents isolated from the stem wood of the African shrub *Combretum caffrum* (Combretaceae) and were initially purified and identified by G. R. Pettit et al. Due to its potent anti-tumor activity in vitro, Combretastatin A4 (CA4) was targeted for further clinical development. In mode of action studies, CA4 was found to compete with Combretastatin A1 as a potent inhibitor of tubulin-binding activity. This suggested an anti-tumor mechanism of action whereby CA4 bound to tubulin polymers and interfered with cell division (U.S. Pat. Nos. 4,996,237, 5,409,953, and 5,561,122, incorporated herein by reference). However, the solubility of CA4 in water was very limited and as a part of its continued development certain prodrug compositions were developed to increase the solubility and thus the efficacy of CA4. The term "prodrug" is used herein to refer to a precursor (exemplified without limitation by metal and amine phosphate salts) of CA4 which will undergo metabolic activation in vivo to the active drug CA4. In particular, CA4 phosphate disodium salt (CA4P) was shown to be readily soluble in water (U.S. Pat. No. 5,561,122) and selectively toxic to tumors. This latter property was subsequently found to have important implications in vascular targeting (see WO 00/48606) as the highly selective tumor toxicity effects of CA4P were further identified to be due to a targeted toxicity towards tumor-associated vasculature and a consequential shutdown of tumor blood flow (Dark et al., Cancer Research 57:1829–1834, 1997; Tozer et al., Cancer Research 59: 1626–1634, 1999).

Because CA4 is not nearly as effective a vascular targeting agent as CA4P (Chaplin et al., Br. J. Cancer 74 (suppl 27): S86–S88, 1996), mode of action studies have focused on CA4P. No one in the scientific community disputes that the vascular targeted toxicity observed with CA4P relates to its tubulin-binding mechanism. In fact, retraction and blebbing of microvessel endothelial cells (HUVEC) which is a manifestation of toxicity associated with apoptosis has been shown to be induced by CA4P (Iyer et al., Cancer Research 58: 4510–4514, 1998). Furthermore, cytoskeletal alterations affecting the dynamics of actin also support this cytotoxic mechanism. In conclusion, there is already established a good rationale for why microvessels can be killed by CA4P and thereby become antitumor agents, but there does not exist any compelling hypothesis as to why tumor endothelia are killed with preference to other cell types. Currently, there are two theories: (i) the expression of alkaline phosphatase is upregulated in these tissues, thus selectively converting more non-cytotoxic, non-tubulin binding prodrug to its cognate cytotoxic, tubulin-binding CA4 form and/or (ii) endothelial cells in tumor vessels of microvessels is selectively different from normal vessels, permitting greater uptake and toxicity of CA4P.

SUMMARY OF THE INVENTION

The present invention provides the use of a low dose of Combretastatin A4 or any of its prodrugs as an enhancer of the anti-tumor immune response. The invention encompasses the unexpected finding that combretastatin A4 has therapeutic utility as a NO reducing agent when used at a dose that is not causing vasculature shut-down. It is an object and advantage of this invention that low-dose CA4P can remove the tumor-induced immunosuppression effects that are problematic for immuno-gene therapy and other therapies. It is also an object and advantage of this invention that low-dose CA4P can be used as a viable anti-tumor treatment with none of the toxicity problems that have been encountered with other treatments.

While the anti-tumor properties of CA4 and CA4P are very different, the present invention embraces the discovery that a low dose of either combretastatin A4 or its prodrug is capable of enhancing immune-directed antitumor activity when given in combination with an immune stimulating therapy. The mechanism to explain these effects is necessarily different than the mechanism resulting in tumor vasculature shut-down. Higher doses (4–100 mg/kg in the rat) of combretastatin A4 prodrug are both toxic to microvessels and immunosuppressive, but at 2 mg/kg there was no obvious toxicity to tumor microvessels and in the presence of immune stimulation therapy the Combretastatin A4 prodrug was immune enhancing. A selective inhibitory effect on certain functions of adherent blood cell sub-types was primarily responsible. These data indicate that this selective effect against certain immune modulating cell sub-types can reduce tumor directed immune suppression causing an enhanced toxicity to tumors and an antiproliferative growth control.

Thus, the present invention, in a first aspect, broadly contemplates the provision of a method of treating a human or other warm blooded animal comprising selectively administering to the subject combretastatin A4 or A4 prodrug material at a dose that is not causing tumor vasculature shut-down but is capable of removing immunosuppressive effects from an immunogenic tumor. Moreover, the immune enhancing effect can be given in combination with other immune therapies, immunotoxin therapy based on bacterial toxins or by itself. The preferred dose schedule is 5 days/week when significant tumor burden is present. The dose levels based on the rat would be in the range of ⅕ to ¹⁄₂₀ the MTD (minimum tolerated dose) or at a dose causing no tumor vasculature shut-down.

Further features and advantages of the invention will be apparent from the detailed description hereinafter set forth, together with the accompanying drawings.

DETAILED DESCRIPTION

Figure 1A:
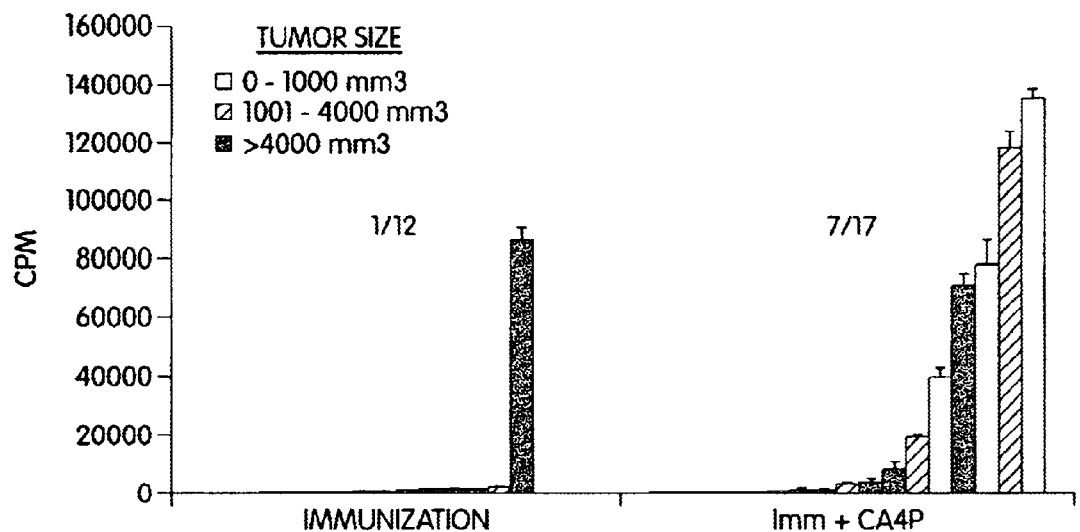
FIGS. 1A and 1B illustrate the enhanced in vitro immune proliferative response of spleen cells isolated from BN7005-H1D2 tumor-bearing rats previously treated in vivo with a combination of active immunomodulatory gene therapy (IL-18 transfected tumor cells) and CA4P (2 mg/kg 5 days a week). The cells were stimulated with IL-18-transfected tumor cells (FIG. 1A) or superantigen SEA (FIG. 1B).

The present invention provides a dose of Combretastatin A4 Prodrug for use as an immune enhancing agent to stimulate the proliferation of anti-tumor T cells in a tumor host. When a low dose of CA4P is administered to an animal bearing a tumor isograft in combination with immunomodulatory gene therapy, anti-tumor cytotoxic T cells (CTLS) are able to clonally proliferate and mount an effective cytolytic immune response against the tumor cells of the isograft. The effect of such activation is the infiltration of activated T cells and macrophages into the tumor mileu and destruction of the tumor by toxic effector mechanisms.

One way to analyze the efficacy of an anti-tumor immune response is to examine in vitro the degree of sensitization of immune cells to a tumor antigen using a Mixed Lymphocyte-Tumor Culture (MLTC) test. In this technique lymphocytes are recovered from a tumor-bearing animal and mixed with autologous tumor cells that have been made incapable of cell division by e.g., X-ray irradiation. Lymphocytes can be obtained from a variety of lymphatic tissues including the spleen, peripheral blood, lymph nodes, or from the tumor tissue itself. One is then able to identify an anti-tumor CTL previously primed or activated by a tumor antigen on the tumor isograft, since it should be responsive to re-stimulation by the same tumor antigen and will proliferate to form an expanded population of identical anti-tumor cells.

The relative number of antitumor T cells can be measured empirically in a Lymphocyte Proliferation Assay which measures the entry of the cells into the DNA Synthesis (S) phase of the cell cycle and reflects the proliferative phase of the T cell response. The amount of radiolabelled DNA synthesis precursor (e.g., $^3$H-thymidine) incorporated from the culture medium is measured. The expanded cell clone can also be assayed for cytotoxic activity based on its ability to lyse the tumor cells in a chromium release assay. Tumor cells are incubated in radioactive chromium ($^{51}$Cr) which is taken up by the cells and bound by cytosolic protein. Unadsorbed radiolabel is washed away and the tumor cells are cultured in the presence of titered CTL. The amount of chromium released into the media then serves as a measure of the number of lyzed tumor cells.

Normally the immune response to tumor challenge is quite weak and CTLs fail to proliferate extensively both in vivo and when tested in vitro. This result has been attributed to the ability of the tumor to escape immune surveillance through the use of an arsenal of decoy mechanisms. In some cases the tumor cell may decrease the availability of an immunogenic tumor antigen to the immune system. Tumor cells may downregulate the expression of the antigen. Alternatively, a tumor cell may shed the tumor antigen completely. In addition, certain tumors may fail to express or poorly express MHC antigens which are required for the presentation of a tumor antigen to a T cell. A second general mechanism of immune system evasion is the ability of a tumor cell to alter the ability of immune system to respond to tumor antigen. Instead of altering antigen expression, the tumor may produce molecules that alter the expression of co-stimulatory molecules on antigen presenting cells, e.g., dendritic cells. Because these costimulatory molecules are required for activation of a T-cell that has recognized its target antigen, tumor cells often fail to activate appropriate T cell clones despite the expression of adequate tumor antigens. This type of immunological suppression can lead to immunological tolerance by making the suppressed T cells incapable of subsequent response to the antigen even in the presence of normally costimulating molecules. This state of tolerance can be broken by signalling via certain key molecules and their receptors/ligands, e.g., CD40, CD134, 4-1BB, present on certain antigen presenting cells and the T cells. Excess amounts of certain cytokines produced by the T cells (IFN-γ, TNF, IL-2) and certain antigen presenting cells (IL-12) can provide compensation for a relative lack of costimulation.

Immunomodulatory gene therapy has received much attention in recent years as a means to enhance the immune response to tumor antigens and guide it towards generation of CTL. This is, in effect, a cancer vaccine, and is a form of active and specific immune therapy. The treatment strategy involves the injection, e.g., into the skin of a tumor host, of a suspension of autologous tumor cells that have been made capable of expressing or producing molecules that stimulate a strong systemic CTL response against the tumor antigens. The technique requires harvesting a sample of the host's own tumor, culturing the cells ex vivo and transfecting with an expression construct capable of facilitating constitutive or inducible expression of the immunomodulatory gene. Such an expression construct can be delivered to the cell in a gene delivery vector such as an attenuated virus or within liposome. After selection of the transfected cells on the basis of a selectable marker on the expression construct, immunomodulatory cancer cells are then expanded to generate sufficient numbers for injection as a live vaccine back into the tumor host after preventing their proliferation by irradiation or chemical treatment. In a variation of this scheme, tumor cells can be directly altered in situ to produce immunomodulatory molecules. Direct injection into the tumor of a liposomal DNA mixture or viral vector (e.g., Adenovirus) serves to expedite the lengthy ex vivo process.

There are two classes of molecules that have received attention for their applications to immunomodulatory gene therapy. One class includes genes which encode costimulatory molecules on the surface of a tumor cell. The most widely studied costimulatory molecules, B7-1 and B7-2, interact with the CD28 receptor on T-cells to enhance T-cell activation. These costimulator molecules cooperate and synergize with other identified costimulator molecules, e.g., CD40, CD134, 4-1BB. The other class includes genes of various cytokines made to be secreted by the tumor cells into the local environment. Cytokines are analogous to immune-specific hormones in that they are capable of stimulating the growth and differentiation of immune cells. Cytokine genes that have been used as candidates for this strategy include IL-1, IL-2, IL-4, IL-6, IL-7, IL-12, IL-18, IFN-γ, GM-CSF. IL-12 and IL-18 have attracted special interest because they augment both T-cell and Natural Killer (NK) cell activity, which can be especially effective anti-tumor effector cells. While both types of molecules have generated some experimental success as monotherapies, co-vaccination strategies markedly enhance anti-tumor activity and may define future approaches to immunomodulatory gene therapy.

Vaccination Response Enhancement

Despite its promise as an effective cancer treatment, immunomodulatory gene therapy is still largely experimental and its development has not yet moved beyond the preclinical stage. There are still a number of hurdles that must be overcome before this type of treatment is a viable option to traditional radio- and chemo-therapies. One major obstacle in this approach is the tumor-induced immunosuppression that tends to spontaneously develop and increase in strength with time and increasing tumor size. T-cells isolated from tumor-bearing mice treated at a later stage when the tumor is larger, fail to respond to tumor cell antigens in both cytolytic and proliferation assays. Often the immunosuppression is fully established during the period of time required for active immunization and serves to limit or abrogate any therapeutic benefit of an immune stimulatory therapy.

Figure 1B:
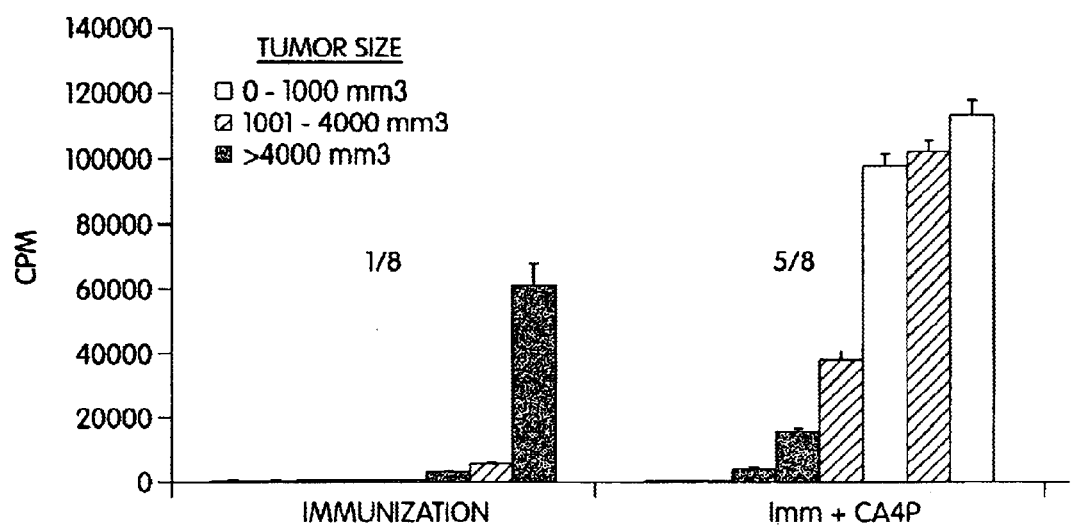

The present invention encompasses the finding that a low dose of CA4P can reverse the effects of tumor-induced immunosuppression when administered to vaccinated tumor bearing animals. The immunomodulatory effects of vaccination by cytokine-transfected tumor cells are significantly augmented by a low dose of CA4P, as demonstrated by its enhancing effects on T-cell proliferative responses in vitro. By way of illustration, as shown in FIG. 1, in a particular embodiment, rats bearing an intrahepatic colon carcinoma were subjected to weekly vaccinations of tumor cells expressing IL-18 or mixtures of cells expressing IL-12 and IL-18. A low dose of CA4P was administered (2 mg/kg, 5 days a week) to a subset of vaccinated animals. Five to 8 weeks after initiation of tumor growth untreated rats were all dead with large tumors. In contrast, most vaccinated animals were not yet dead but were burdened with tumors of relatively large size. Spleen immune cells, including adherent macrophages, were isolated from these animals and tested in an in vitro proliferation assay. In one experiment, as shown in FIG. 1A, the isolated immune cells were stimulated with autologous tumor cells. Whereas spleen cells of only one of 13 (8%) animals treated with immunization alone responded to tumor antigen challenge, 7 of 18 samples (39%) from CA4P-treated animals responded, including 5 of 6 animals showing the strongest CA4P growth inhibitory effects (tumor sizes<4 cm$^3$). This difference was even more apparent when the superantigen polyclonal T cell activator, Staphylococcal Enterotoxin A (SEA) was used to challenge the spleen cells (FIG. 1B). Five of 8 (63%) CA4P treated rats responded to SEA, while only one of 8 (13%) untreated rats responded. All 4 animals with the strongest tumor growth inhibitory effect of CA4P responded.

Immune Enhancement: Criticality of Dosage

Figure 2A:
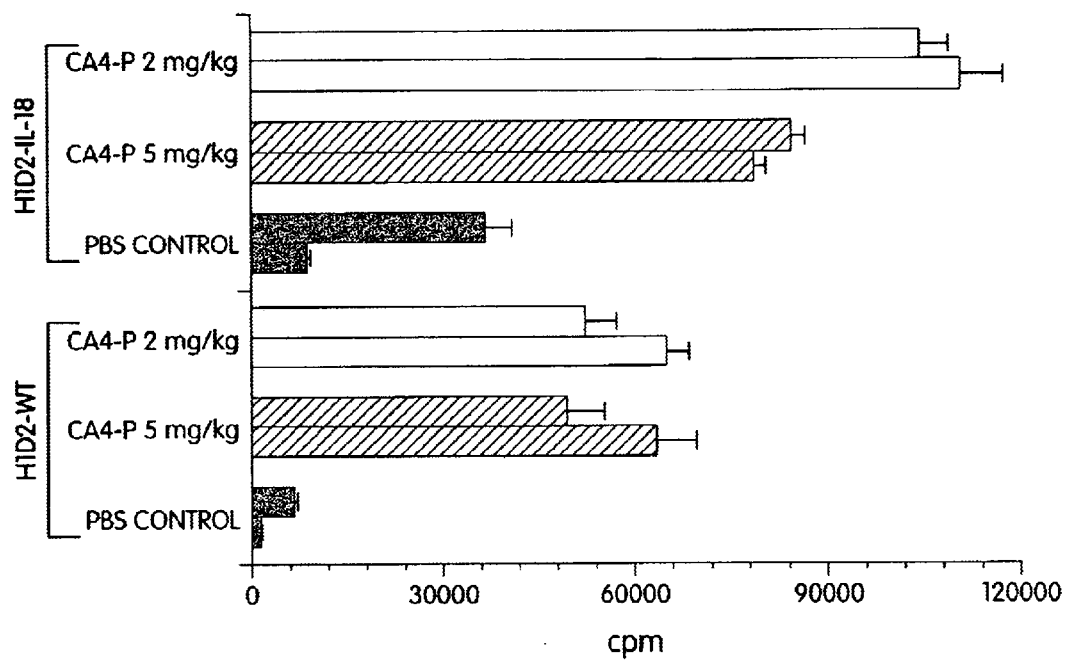
FIG. 2A illustrates the in vitro immune proliferative response of spleen cells isolated from BN7005-H1D2 tumor-bearing rats previously treated with a combination of active immunomodulatory gene therapy (IL-18 and IL-12 transfected tumor cells) and CA4P (5 or 2 mg/kg) in vivo. The cells were stimulated with untransfected (H1D2-WT) tumor cells or IL-18 (H1D2-IL18) transfected tumor cells after 20 days of tumor growth.
Figure 2B:
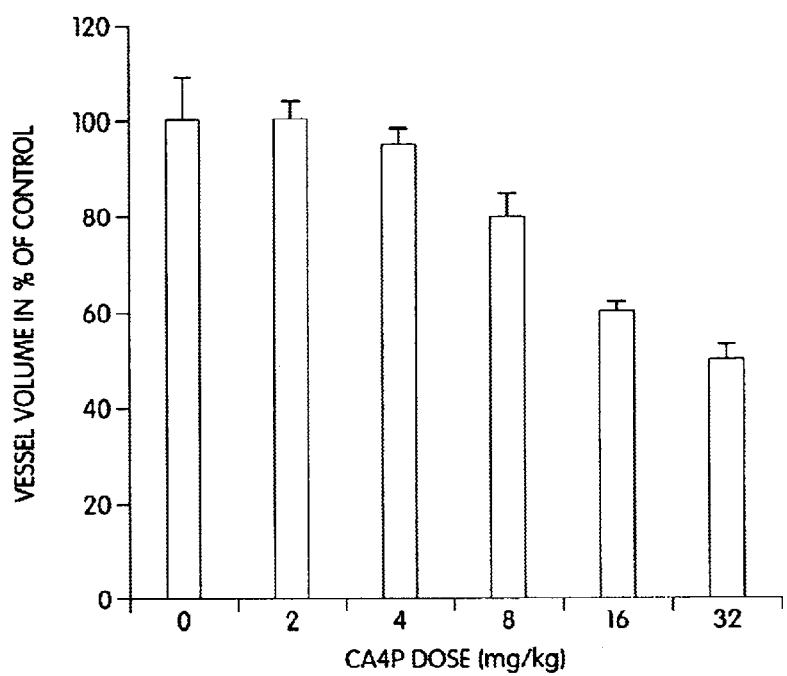
FIG. 2B illustrates the percentage of open tumor blood vessels in an excised tumor 24 hours after administration of various doses of CA4P to a BT4Cn tumor bearing rat.

Results of in vitro studies indicate that the dose of Combretastatin A4 Prodrug that is administered is critical for obtaining a specific immunological effect. The specific immunomodulatory properties of CA4P are only observed at a low dosage, whereas higher doses fail to remove the immunosuppressive effects of the established tumor or induce suppression of lymphocyte activity. As shown in FIG. 2A, spleen cells of 2 PBS treated control rats, 2 rats treated with 5 mg/kg CA4P, and 2 rats treated with 2 mg/kg CA4P were tested in vitro for proliferative response to tumor wild type (H1D2-WT) or IL-18 transfectant stimulator cells after 20 days of daily treatment. Proliferation of spleen immune cells was monitored by 3-H-thymidine incorporation (CPM) after 5 days incubation. While some enhancement of a proliferative response was observed with 5 mg/kg of CA4P, a dose of 2 mg/kg was particularly effective in enhancing the anti-tumor immune response. Of particular significance, is the fact that no vascular shut down could be observed in rats treated with 2 mg/kg. As FIG. 2B demonstrates, there is no significant vascular shutdown of CA4P in doses below 4 mg/kg. An analysis of tumor pathology was performed on BT4Cn tumor-bearing rats when the tumor had growth to a size of 300 mm$^3$. Rats received single intraperitoneal injections of various doses of CA4P. Twenty-four hours later they were injected with 0.25 ml of Fluo-Spheres bead in the tail vein and sacrificed after 3 min. Tumors were removed and prepared for cryosection. Eight μm cryosections were examined directly in a fluorescence microscope and vessel volume was determined (Springer, MP., Ip, TK., and Blau, HM). Angiogenesis monitored by perfusion with space-filling microbead suspension (Mol. Ther. 1: 82–87, 2000). The results of this experiment clearly indicated that any immune modulating effects of low dose CA4P were not secondary to vascular shut down. In addition, IL-18 transfectant stimulator cells were more effective at enhancing the immune response than wild-type cells, supporting the interpretation that the response was a true immune modulating effect. Thus in a preferred embodiment, the dose at which CA4P is administered to achieve a desired immune enhancing effect without vascular shutdown is less than 5 mg/kg.

Mechanism of Low-Dose CA4P Immune Enhancement

The limited success obtained with immunomodulatory gene therapy tends to indicate that understanding the mechanisms of tumor-induced and therapy-induced immunosuppression may be crucial for development of effective immunotherapy. Research in this field has already revealed much about these phenomena. It is well known that tumors are able to secrete a number of immunosuppressive molecules, including transforming growth factor-beta (TGF-β), IL-10, and prostaglandin E2 (PGE2) which play a role in tumor-induced immunosuppression. With several types of tumors, however, the development of immunosuppression to a large extent appears to be due to overproduction of immunosuppressive factors by macrophages. Overproduction of Nitric Oxide, oxygen radicals, PGE2, and IL-10 by tumor-induced macrophages have been shown to inhibit the function of T-cells, despite the fact that NO and oxygen radicals are also important mediators of anti-tumor effects when produced at lower levels. A strong immunosuppression of this type has been demonstrated to develop in the course of intrahepatic growth of rat colon carcinoma and at a lower level in tumor-free animals as a result of vaccination with tumor cells producing IL-12, IL-18 and IFN-γ, which cytokines are known inducers of NO and oxygen radicals.

Therefore, there is an urgent need of a means to inhibit or interfere with these processes which are hurdles to acceptance of immunomodulatory gene therapy as a viable cancer therapy. The present invention additionally embraces the discovery that a low dose of CA4P has a specific effect of reducing tumor induced macrophage immunosuppression. This newly discovered property of CA4P is particularly nonobvious when one considers that the generally accepted mechanism of action of CA4P is via inhibition of growing endothelial cells present preferentially in tumor tissue resulting in vasculature shut down. The lack of a tumor vascular shut-down with a low dose of CA4P (<4 mg/kg) suggests that its immunomodulatory effect occurs by a novel mechanism.

As shown in TABLE 1, the invention provides what type of immune cells are most prominently involved in the immune stimulation induced by combretastatin A4 prodrug. Macrophages were isolated as plastic-adherent spleen cells from tumor-free rats vaccinated with IL-18 and IL-12 transfected tumor cells. Preincubation of the adherent cells (i.e. spleen macrophages) with CA4P resulted in a 2-fold enhancement of the subsequent in vitro proliferative response of admixed non-adherent cells (i.e. T cells) in this experiment. This effect is interpreted as due to a decrease of the suppressive effect of IL-12 and IL-18 activated macrophages on T cell responses.

TABLE 1

Effect of CA4-P on the proliferative T cell response to SEA (Staphylococcal Enterotoxin A) and on NO production by adherent spleen cells of tumor-free rats immunized with colon carcinoma cells after transfection (BN7005-H1D2-IL-12 and IL-18) as previously described (Hegardt et al, (2001) Cancer Immunol Immunother 50:491–501)

|  |  | Rat#1 CA4P[1] | | Rat#2 CA4P[1] | |
|---|---|---|---|---|---|
|  |  | − | + | − | + |
| Proliferative T cell response[2] (CPM thymidine incorporation): | | | | | |
| L1[3] | SEA MO[3] | 50K | 124K | 8 | 22 |
| Nitric acid production[4] into supernatant (μM): | | | | | |
| L0 | SEA | 15 | 8 | 19 | 7 |
| L0 | Medium | 14 | 7 | 18 | 6 |

[1]Adherent spleen cells (MO or unseparated spleen cells (L0) were preincubated for 3 h with or without CA4-P (0.15 μg/ml) before addition of nonadherent spleen cells and the T cell stimulator SEA (0.05 ng/ml) and incubation for 4 days at 37° C.
[2]The proliferative T cell response was evaluated by adding 3H-labeled thymidine to the cultures after 4 days of culture and measuring of thymidine incorporation during a 6 h period as previously described (Hegardt et al, (2001) Cell Immunol 200,116).
[3]Adherent spleen cells (MO) were separated by adding spleen cells to 96-well microplates and allowing adherent cells (most of the macrophages) to adhere for 3 h after which nonadherent cells were rinsed off. Nonadherent spleen cells (L1) were separated by allowing adherent spleen cells to adhere for 2 × 45 minutes, collecting nonadherent cells after 45 minutes and continuing incubation for another 45 minutes in anew plastic culture bottle (50 × 10$^6$ cells per 175 cm$^2$ plastic area).
[4]Nitric acid (NO) production was evaluated by the Griess technique (Green et al (1982) Anal Biochem 126, 131).

Figure 3A:
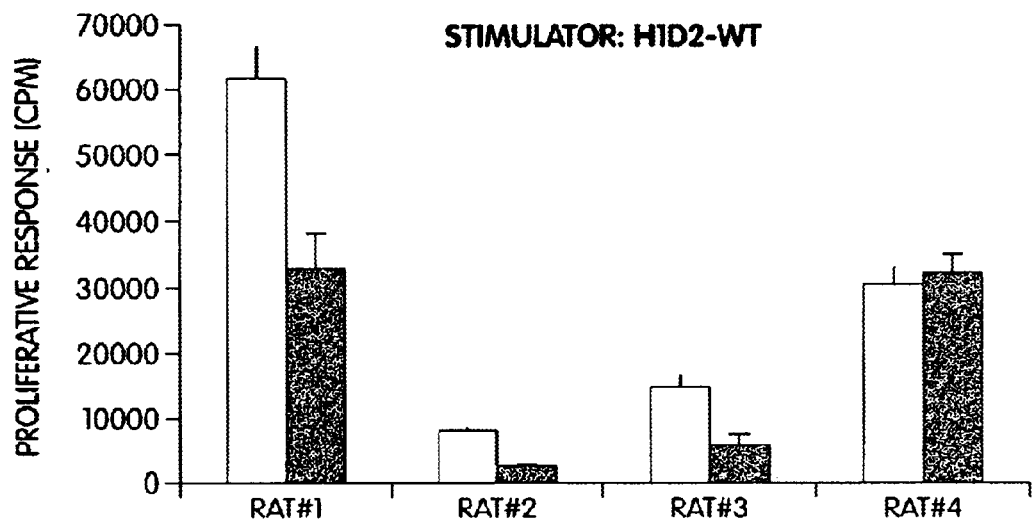
FIGS. 3A, 3B and 3C illustrate the in vitro immune proliferative response of unseparated spleen cells isolated from tumor-free rats previously vaccinated with IL-18 and IL-12 transfected tumor cells. Spleen cells were stimulated with untransfected (H1D2-WT) tumor cells (FIG. 3A) or the super-antigen SEA polyclonal activator (FIG. 3B) after preincubation with or without CA4-P (0.15 ug/ml). NO production (FIG. 3C) was also measured in SEA-stimulated spleen cell cultures following preincubation with or without CA4P (0.15 ug/ml).
Figure 3B:
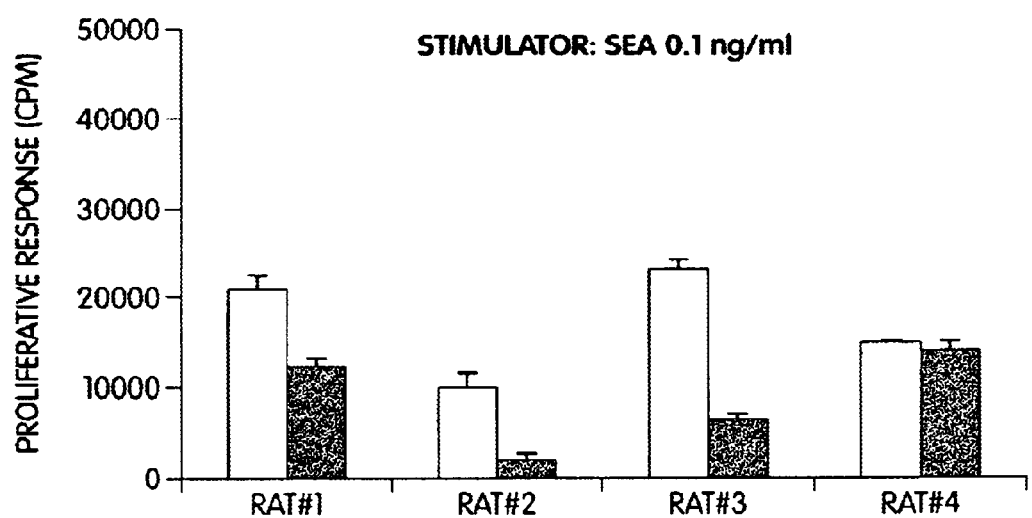
Figure 3C:
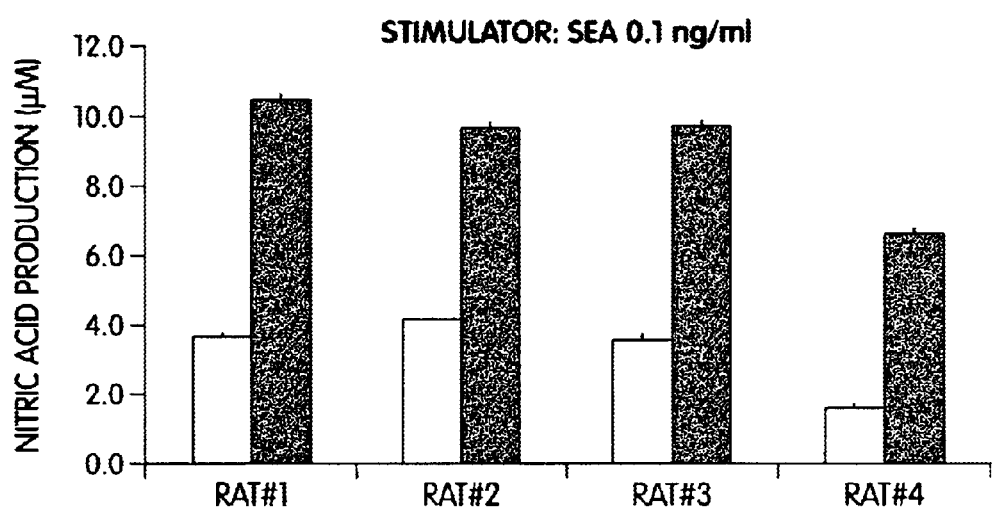

The observation of selective macrophage toxicity is further supported by the observation that CA4P treatment of unseparated spleen cells recapitulates this anti-tumor immune response. FIG. 3 illustrates the in vitro immune proliferative response of unseparated spleen cells isolated from tumor-free rats previously vaccinated with IL-18 and IL-12 transfected tumor cells. Spleen cells were stimulated with untransfected (H1D2-WT) tumor cells (FIG. 3A) or the superantigen SEA polyclonal activator (FIG. 3B) after preincubation with or without CA4P (0.15 μg/ml). The fact that the T cell segment of the spleen cell population is capable of responding to immune stimulation suggests that the low dose CA4P is selectively toxic to the macrophage population of cells and not to the T cells themselves.

One of the main suppressive molecules produced by macrophages is nitric oxide (NO) and direct assays of the generation of NO released into the medium of parallel spleen cell cultures (containing both adherent and nonadherent cells) after exposure to SEA and CA4P were performed as previously described (Hegardt et al, Cancer Immunol & Immunother (2001) 50: 491–501). CA4P induced a significant reduction of NO produced in 2 animals studied (TABLE 2 and FIG. 3C). Similar parallel studies of the effect of CA4P on the proliferation response of spleen cells stimulated with wild type tumor cells and SEA (0.1 ng/ml), respectively, showed a stimulating effect on the proliferative response in 3 of 4 animals and an inhibitory effect on NO production in all 4 rats.

It is believed that the production of immunosuppressive molecules (NO, Oxygen radicals, PGE2, and IL-10) is a normal function of macrophages. An increased production of these molecules is induced at activation of the macrophages, although the relative amount of each molecule is not necessarily the same but is determined by the cytokine milieu and other factors. A main activator of macrophages is IFN-γ and the cytokines IL-12 and IL-18 that in turn induce IFN-γ. This activation normally results in maturation of the macrophages into cytolytic effector cells. Alternatively, the prolonged activation may lead to arrested development and sustained production of the molecules normally produced only at activation. In tumor-bearing animals, there is a known increase in macrophage NO production and sometimes of PGE2. Therefore, the demonstrated capacity of CA4P to inhibit NO production in tumor-free vaccinated rats is a relevant predictor of effect of CA4P on tumor-bearer macrophages. In addition, these experiments indicate that CA4P counteracts the generation of increased levels of IFN-γ, which can be toxic.

Equivalent Immune Modulatory Properties of Low Dose CA4 and CA4P

Due to problems with the insolubility of its parent compound, CA4P was synthesized as a disodium phosphate analog of CA4. In addition to improved aqueous solubility, CA4P had the unexpected property of selective tumor toxicity. Further investigations revealed that the selectivity of CA4P was due to a targeted toxicity towards tumor-associated vasculature which resulted in the destruction of the vasculature and a consequential shutdown of tumor blood flow. Because of its novel function as a vascular targeting agent (VTA), mode of action studies have focused on CA4P rather than CA4. In particular, these studies have examined how the phosphate moiety of CA4P imparts a vascular targeting property to CA4. In addition, a variety of phosphate salts other than disodium phosphate, including metal and amine salts, have been investigated for further improvements in anti-tumor vascular targeting activity (WO 99/35150).

Figure 4:
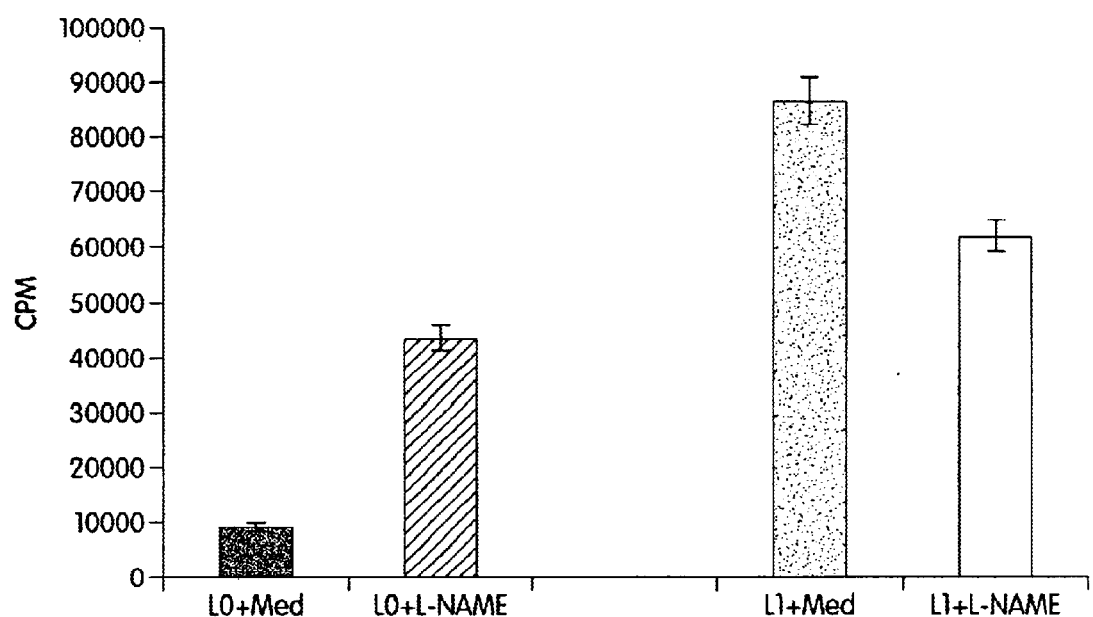
FIG. 4 illustrates the enhanced in vitro immune proliferative response (cpm) of spleen cells isolated from (H1D2-WT) a tumor-bearing rat previously treated in vivo with a combination of active immunomodulatory therapy and CA4 (2 mg/kg, 6 days a week). Spleen cells were tested 9 weeks after tumor inoculation when tumor sizes was 0.9 cm$^3$. LO signifies spleen cells containing adherent macrophages, whereas L1 represents the same population depleted of adherent macrophages. A subset of each cell sample was treated with either medium (Med) or L-NAME (1.5 mg/ml).

While the anti-tumor properties of CA4 and CA4P are very different, the present invention embraces the discovery that a low dose of either compound is capable of enhancing the immune responsiveness of a tumor host. FIG. 4 illustrates the in vitro immune proliferation of spleen cells isolated from a tumor-bearing rat previously subjected to treatment with a combination of CA4 (2 mg/kg) and active immunotherapy. The rat was killed 9 weeks after initiation of intrahepatic tumor growth, at which point the tumor had grown to a size of 0.9 cm$^3$. Control rats receiving immunotherapy alone were euthanized 5 weeks earlier due to the development of large tumor burdens (>5 cm3). The CA4-treated rat had a detectable and significant T cell proliferative response (9000 cpm for unseparated spleen cells (L0) and 86,000 cpm for non-adherent T cells (L1), indicating a strong anti-tumor T cell response that was only partially inhibited by macrophage-mediated suppressive molecules. The response of the unseparated spleen cells was further enhanced (44,000 cpm) in the presence of the Nitric Oxide Synthase (NOS) inhibitor L-NAME, indicating that NO was a major suppressive factor.

FIG. 4 demonstrates that, similar to CA4P, a 2 mg/kg dose of CA4 is capable of enhancing anti-tumor immune responsiveness in vitro. As is the case with CA4P, the mechanism to explain these effects is necessarily different than the mechanism resulting in tumor vasculature shut-down, since CA4 is not capable of a selective vascular targeting effect, regardless of dose. Instead, the mechanism of CA4 immune enhancement is primarily due to the reversal of the immunosuppressive effects of macrophage-produced NO. Therefore, the property of immune enhancement is shared by low dose CA4 and CA4P and is a property inherent to the core structure or nucleus of the molecule which is shared by both CA4 and CA4P, and is expected to be a property of any other combretastatin-A4 phosphate salt, including without limitation, the amine and metal phosphate salts of CA4P which are embodiments within the scope of the invention.

Effect of Low-Dose CA4 and its Prodrugs on Tumor Growth

In some immunomodulatory gene therapy studies antitumor activity is only active against relatively low tumor burdens, predicting a potential difficulty in treating patients with large volume tumors and established metastatic disease. There is a need in the art for an agent which would limit the growth of the tumor and allow for the host immune system to mount an effective immune response following vaccination. The present invention further provides a dose of CA4P that is able to inhibit the growth of a tumor mass in vivo during the time of immunomodulatory gene therapy. As shown in TABLE 2, CA4P has a distinct growth inhibitory effect in vivo when administered at low dosage (5 or 2 mg/kg) in combination with active immunotherapy. In contrast with in vitro immune proliferative experiments, there are a higher range of doses that impart tumor growth inhibition and this effect is enhanced at higher doses. In particular, the enhanced effect on tumor retardation with a 5 mg/kg dose is most likely explained by an additional effect on vascular shutdown which is not observed at a dose of 2 mg/kg. Additional growth inhibition was achieved by concurrent treatment with the nitric oxide synthase (NOS) inhibitor L-NAME or L-NAME combined with the prostaglandin inhibitor Indomethacin.

TABLE 2

Summary of repeat experiments with intrahepatic growth of colon carcinoma H1D2-WT cells testing the therapeutic effect of low dose CA4-P alone or in combination with therapeutic immunization with tumor cell transfectants (H1D2-IL-18) with or without additional treatment with the NOS-inhibitor L-NAME(+Indomethacin)

| CA4-P mg/kg | L-NAME gavage | Immunization | N | Mean | SEM | Median | Significance of difference to control |
|---|---|---|---|---|---|---|---|
| 5 | - | + | 5 | 1499 ± | 289 | 1254 | 0.004 |
| — | - | + | 5 | 4688 ± | 729 | 4586 | — |
| 5 | - | + | 6 | 1732 ± | 453 | 1374 | 0.004 |
| 2 | - | + | 6 | 3918 ± | 435 | 3780 | 0.05 |
| — | - | + | 6 | 6061 ± | 1043 | 6626 | — |
| 5 | + | + | 5 | 512 ± | 99 | 426 | 0.007 |
| 5 | - | + | 6 | 754 ± | 172 | 610 | 0.009 |
| — | - | + | 6 | 5082 ± | 1258 | 5551 | — |
| 2 | + | + | 6 | 5064 ± | 714 | 4792 | 0.003 |
| 2 | - | + | 6 | 5755 ± | 809 | 6195 | 0.005 |
| — | - | + | 6 | 10200 ± | 1225 | 10773 | — |
| 5 | + | + | 3 | 561 ± | 199 | 367 | <0.0001 |
| — | + | + | 5 | 1285 ± | 482 | 879 | 0.0003 |
| — | - | - | 5 | 4891 ± | 259 | 4896 | — |
| 2 | +(+INDO) | + | 4 | 2835 ± | 165 | 2867 | 0.0006 (0.02) |
| 2 | - | + | 4 | 5135 ± | 1127 | 4275 | 0.02 |
| — | - | - | 4 | 8952 ± | 607 | 9322 | — |
| 2 | +(+INDO) | + | 4 | 1397 ± | 105 | 1463 | 0.002 (0.01) |
| 2 | - | + | 4 | 3698 ± | 488 | 3393 | 0.004 |
| — | - | - | 4 | 7252 ± | 692 | 7242 | — |

TABLE 2-continued

Summary of repeat experiments with intrahepatic growth of colon carcinoma H1D2-WT
cells testing the therapeutic effect of low dose
CA4-P alone or in combination with therapeutic immunization with
tumor cell transfectants (H1D2-IL-18) with or without additional treatment
with the NOS-inhibitor L-NAME(+Indomethacin)

| CA4-P mg/kg | L-NAME gavage | Immuniza-tion | N | Mean | SEM | Median | Significance of difference to control |
|---|---|---|---|---|---|---|---|
| 2 | +(+INDO) | + | 4 | 1977 ± | 486 | 1962 | 0.001 (0.01) |
| 2 | – | – | 4 | 3834 ± | 348 | 4037 | 0.003 |
| — | – | – | 4 | 6266 ± | 432 | 6031 | — |

Drug administering (CA4-P, L-NAME, Indomethacin) was initiated 7–8 days after placing $1 \times 10^5$ in vitro cultured H1D2-wild type cells contained in 50 µl medium beneath the liver capsule. CA4-P was given i.p. 5 days a week, L-NAME twice a week on the day of immunization and the day after, and Indomethacin was given 48 h after vaccination 0.33 mg/kg. Immunization was performed intraperitoneally with IL-18 transfectants of H1D2 tumor cells or a mixture of IL-18 and IL-12 transfectants (2–3 × $10^6$ viable cells per rat).

Table 2 is a summary of intrahepatic growth of colon carcinoma H1D2-WT cells treated with low dose CA4P alone or in combination with immunomodulatory gene therapy, and with or without additional inhibitor. Tumor growth was initiated by inoculation beneath the liver capsule with $1\times10^5$ in vitro cultured BN7005-H1D2 wild type cells suspended in 50 µl RPMI medium. Drug administration (CA4P, L-NAME, Indomethacin) was initiated after 7–8 days when the tumor was macroscopically visible. CA4P was given intraperitoneally, 5 days a week. L-NAME was given by gavage twice a week on the day of immunization and the day after. Indomethacin was given by gavage 48 h after vaccination at a dose of 0.33 mg/kg. Immunization was performed by intraperitoneal administration on day 10 and day 17 using BN7005-H1D2 cells transfected with IL-18 or a mixture of IL-18 and IL-12 transfectants (2–3×$10^6$ viable cells per rat).

Figure 5A:
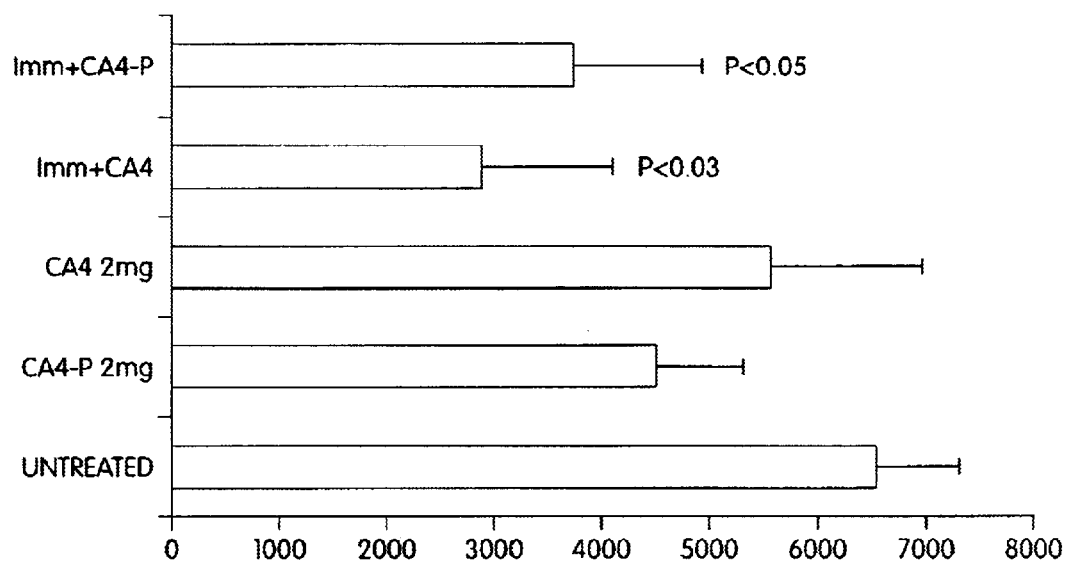
FIGS. 5A AND 5B illustrate a comparison of the therapeutic effect of Combretastatin A4 and Combretastatin A4 Prodrug (2 mg/kg) on tumor growth (BN7005-H1D2) in vivo as a sole therapy or in combination with therapeutic vaccination (IL-18 tumor transfectants). Results are represented as mean tumor volume (FIG. 5A) or as median tumor volume (FIG. 5B) 31 days after tumor initiation.
Figure 5B:
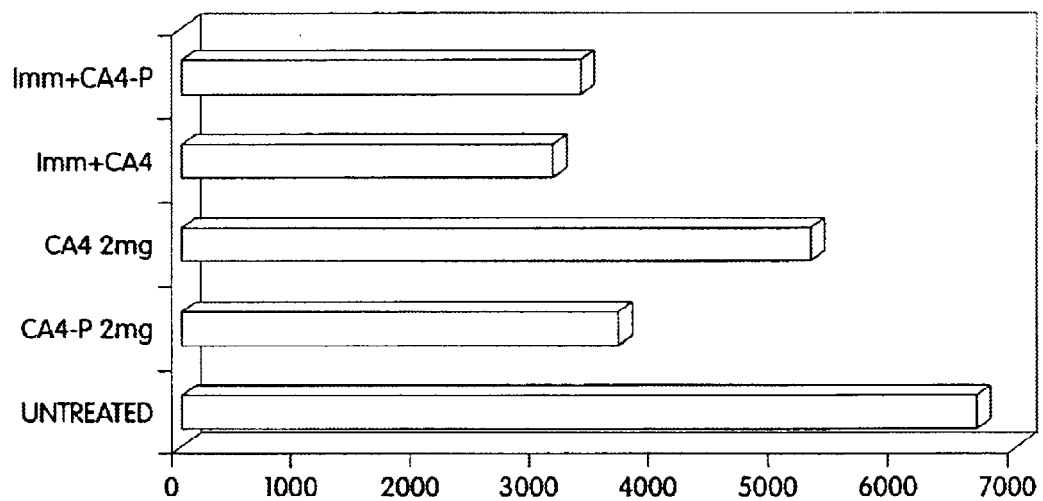

A comparison was also made of relative effect of CA4 and CA4P administration in vivo with regard to tumor inhibitory effects when used as sole therapy and when combined with immunomodulatory gene therapy. As illustrated in FIG. 5, regular treatment of a BN7005-H1D2 tumor-bearing rat with CA4 and CA4P (2 mg/kg) began when the tumors were macroscopically visible. A subset of these animals were subjected to regular vaccinations autologous IL-18 and IL-12-transfected tumor cells, respectively. The data clearly showed that both CA4 and CA4P have similar, significant tumor inhibitory effects when combined with vaccination but not as sole therapy at this low dosage. Since CA4 has been shown to lack or have significantly lower capacity than CA4P to induce vascular shut-down, the tumor inhibiting effect of CA4 when combined with immunotherapy was taken as evidence that immune enhancing therapy was enhanced by combretastatin A4 in a similar way as by CA4 prodrug.

Alternative Embodiments of the Invention

The competitive NOS inhibitor L-NAME has previously been shown to reduce the suppressive effect of tumor bearer macrophages. However, this invention embraces the further discovery that a combination treatment of CA4 or its prodrugs along with L-NAME has an additive growth inhibitory effect on tumors in vivo and enhances the anti-tumor T-cell response further compared to either treatment alone (TABLE 1 and FIG. 4). An alternative embodiment of the invention is envisioned where CA4P is administered in combination with iNOS-selective inhibitors (eg. L-NIL (chemical name L-N6-(1-Iminoethyl)-L-lysine) or prostaglandin inhibitors (eg. Indomethacin). This could reduce the side effects due to inhibition of the alternate neural (nNOS) and (eNOS) isoforms that is an unwanted effect of many of NOS inhibitors. Use of this combination may allow for a more complete and selective inhibition of NO synthesis by macrophages. In still another alternative embodiment, CA4P may be incorporated into particles that could be efficiently phagocytosed and as a consequence preferentially reach macrophages and granulocytes and achieve a more complete counteraction of the immunosuppressive effects of these cells.

The following examples are given for the purpose of illustrating the present invention:

EXAMPLE 1

Enhanced Vaccination Response with CA4P Treatment

As described in FIG. 1 and FIG. 2A, a low dose of CA4P can effectively enhance the anti-tumor immune response that is stimulated by immunomodulatory gene therapy and reduce tumor-induced immunosuppression. In both experiments, a murine model was generated bearing an allogeneic intrahepatic tumor (as described in Hegardt et al, supra, 2001). Highly inbred rats (BN×WF) of the F1 cross between the inbred stains BN (Brown Norwegian) and W/F (Wistar/Furth) were used as tumor hosts. Parental tumor cells were obtained as a H1D2 clone by limiting dilution of BN7005 rat colon carcinoma in the absence of selection pressure. Cells (3×105/50 ul) were washed once and suspended in RPMI-1640 medium supplemented with 1% serum of BN rats before inoculation below the liver capsule. A subset of these cells were transfected with a retroviral pLXSN plasmid vector construct containing rat IL-18 or IL-12 and selected as high expression cell clones (H1D1-IL-18 or H1D1-IL-12). After 1 week, when the inoculated tumor cells had developed into a macroscopically viable tumor, aliquots of 2×$10^6$ transfected tumor cells were injected intraperitoneally to vaccinate the tumor host. Rats were vaccinated again one week later.

In one experiment represented in FIG. 1, 8 of 16 rats were additionally treated 5 days a week with 2 mg/kg of CA4P. Five to 8 weeks later, when control animals were all dead, spleen cells were isolated from all 16 immunized animals and the size of each animal's tumor was measured. Spleen cell (3×105 cells) immune proliferative response was measured in an in vitro immune proliferation assay using 1.5× $10^4$ irradiated H1D1-IL-18 tumor cells (FIG. 1A) or 0.1 ng Staphylococcal Enterotoxin A (FIG. 1B) as the source of stimulator antigen. After 5 and 4 days of incubation respectively, tritiated thymidine was added for 6 hours before cell-associated radioactivity was measured. With both types of stimulating antigen, CA4P treatment resulted in a stronger response to antigen challenge in a larger proportion of samples.

In a second experiment represented in FIG. 2A, wild type H1D2-WT or IL-18 transfected (H1D2-IL-18) cells were used as immune stimulants to assess the in vitro proliferative response of spleen cells isolated from tumor-bearing rats previously treated in vivo with 2 or 5 mg/kg combretastatin A4 prodrug for 20 days. The spleen cells were cultured in RPMI medium and their growth monitored by the incorporation of tritiated thymidine into DNA. First of all, splenic cells from rats treated with both 2 and 5 mg/kg combretastatin A4 prodrug in vivo showed an enhanced proliferative response for both wild type and IL-18 transfected stimulated cellular responses. These data are highly significant because no tumor vascular shut-down could be observed in rats treated with 2 mg/kg (FIG. 2B), hence indicating that any immune modulating effects were independent and not secondary to a vascular shut-down. Secondly, IL-18 transfectant stimulator cells were more effective at enhancing the immune response than wild type cells supporting the interpretation that the response was a true immune modulating effect. Thirdly, the immune modulation was biologically relevant because it was produced under in vivo conditions, ruling out the possibility of an in vitro artifact.

EXAMPLE 2

Mechanism of CA4P Immune Modulation

As described in Table 1, spleen cells were isolated from tumor-free BN×WF hybrid rats immunized twice (1 week between vaccinations) with BN7005-H1D2 tumor cells producing IL-18 and IL-12, respectively. Macrophages were isolated from the sample by allowing isolated spleen cells to adhere to the plastic surface of 96-well microtiter plates, at which point the non-adherent cells were removed.

The purified adherent cells ($6 \times 10^5$/microtiter well) were treated in vitro for 3 hours with 0.15 ug/ml CA4P before washing. This dosage was chosen to reflect the fact that the half-life of CA4P in vivo is less than 15 min., and the extracellular fluid in which it is diluted (blood and interstitial fluid) is known to be about 16.6% of body weight. These variables were used to choose an in vitro concentration that is equal to the average concentration in vivo after a 3 hour period. For example, after treatment with 2 mg/kg in vivo, the concentration would be a maximum of 0.18 ug/ml 1.5 hours later, and less than 1 ng/ml after 3 hours.

The proliferative response of $3 \times 10^5$ admixed non-adherent cells (e.g. T-cells) stimulated for 4 days with SEA (0.05 ng/ml) was estimated as in Example 1. Preincubation of the adherent cells (i.e. spleen macrophages) with combretastatin A4 prodrug resulted in a 2-fold enhancement of the subsequent response of admixed non-adherent cells (i.e. T cells) in this experiment (TABLE 2). This effect is interpreted as due to a decrease of the suppressive effect of the IL-12 and IL-18 activated macrophages on T cell responses. Direct assays of the generation of NO released into the medium of parallel adherent spleen cell cultures after exposure to SEA and CA4P were performed as previously described (Hegardt et al, 2001). CA4P induced a significant reduction of NO produced in 2 animals studied (Table 2). Similar parallel studies (FIG. 3) of the effect of CA4P on the proliferation response of spleen cells stimulated with wild type tumor cells and SEA (0.1 ng/ml), respectively, showed a stimulating effect on the proliferative response in 3 of 4 animals and an inhibitory effect on NO production in all 4 rats.

EXAMPLE 3

Enhanced Anti-Tumor Immune Response with CA4

As demonstrated in FIG. 4, in addition to CA4P, CA4 treatment can also result in an enhanced anti-tumor immune response. A tumor-bearing rat (H1D1-WT) was treated in vivo with weekly immunizations of IL-18 transfected tumor cells (H1D1-IL-18), in addition to CA4 treatment (2 mg/kg) 6 days a week. Due to the inherent insolubility of CA4, the compound the CA4-treated rat (0.9 cm$^3$ tumor) following 59 days of growth, at which point the untreated control rats were all dead with large tumor burdens (>5 cm$^3$) and would not be expected to show an immune response at such a late stage. Both unseparated spleen cells (L0) and nonadherent spleen cells (L1), depleted of most macrophages by plastic adherence (as in Example 2), were tested for a proliferative response to H1D2-IL18 tumor stimulator cells in the absence or presence of the NO-synthase inhibitor L-NAME. The CA4-treated rat had a clearly demonstrable proliferative anti-tumor response, even in the presence of suppressive macrophages, and this effect was significantly enhanced in the presence of L-NAME. These results indicate that there is no major difference between the effects of CA4 and CA4P and their capacity to counteract the immunosuppressive effect of spleen macrophages from tumor bearers.

EXAMPLE 4

Tumor Growth Inhibition

As demonstrated in TABLE 2, CA4P has a direct effect of tumor growth inhibition. Wild-type (BN7005-H1D2) colon cancer cells (1×105 cells) were inoculated intrahepatically and CA4P drug treatment (2 and 5 mg/kg) began daily when the tumors were macroscopically visible. On day 10 and 17, vaccinations were administered intraperitoneally using BN7002-H1D2 cells transfected with IL-18 transfected cells or mixtures of IL-18 and IL-12 transfected cells (2–3×10$^6$ viable cells per rat). L-NAME and Indomethacin were also administered by gavage 48 h after vaccination at a dose of 0.33 mg/kg. The data clearly showed that both L-NAME and CA4P were effective in inhibiting tumor growth.

A comparison has been made of the effect of CA4 and CA4 prodrug with regard to tumor inhibitory effects when used as sole therapy and when combined with immunomodulatory gene therapy. As represented in FIG. 5, wild-type (BN7005-H1D2) colon cancer cells were inoculated intrahepatically and treatment with CA4 and CA4P began on day 7 (2 mg/kg 6 days a week), when the tumors were macroscopically visible. On day 9, 16 and 23, vaccinations occurred using BN7005-H1D2 cells transfected with ILI8 and IL-12, respectively. The data clearly showed that both CA4 and combretastatin A4 prodrug were effective enhancers of immune stimulated gene therapy but had no significant effect as sole therapy in this experiment. Since CA4 has been shown to lack or have significantly lower capacity than CA4P to induce vascular shut-down, the tumor inhibiting effect of CA4 when combined with immunotherapy was taken as evidence that immune enhancing therapy was enhanced CA4 in a similar way CA4P.

EXAMPLE 5

Vaccination Response Enhancement.

Four groups of 6 rats each were inoculated intrahepatically with $1\times10^5$ wild type colon cancer cells (BN7005-H1D2) on day 0. Drug treatment was initiated on day 7, when the tumor was macroscopically visible as a small nodule, and was repeated 5 days a week. CA4-P was administered i.p. at a dose of 5 mg/kg and L-NAME by gavage at a dose of 48 mg/rat. Vaccination was given twice i.p. on day 10.and 17 with $2\times10^6$ tumor cells producing IL-18 and IFN-γ, respectively. No drug treatment was given on the day of vaccination and the day after. On day 28 all animals were laparotomized and tumor diameters measured (the longest diameter (a) and the one perpendicular to the first (b) and tumor volume calculated according to the formula 0.4×a×b×b.

Enhanced Antitumor Immune Proliferative Response.

Spleen cells of 2 PBS treated controls, 2 rats treated with 5 mg/kg and 2 rats treated with 2 mg/kg were tested in vitro for proliferative response to tumor wild type (H1D2-WT) or IL-18 transfectant stimulator cells after 20 days of daily treatment with combretastain A4 prodrug (5 or 2 mg/kg). 3-H-thymidine incorporation (CPM) was measured after 5 days incubation. Mean CPM±SEM is indicated for each animal.

Adherent Spleen Cell (Macrophages) Sensitivity to Combretastatin A4 Prodrug.

Adherent spleen cells of tumor bearers, 10 days after immunization with tumor cells producing IL-18, were obtained in 96-well-plates by incubation of $6\times10^6$ spleen cells for 3 h and washing off the non-adherent cells. CA4-P at various concentrations from 0–0.3 micrograms/ml was added to the adherent cells and incubated for 3 h followed by washing and addition of spleen lymphocytes of the same donors.

Figure 6:
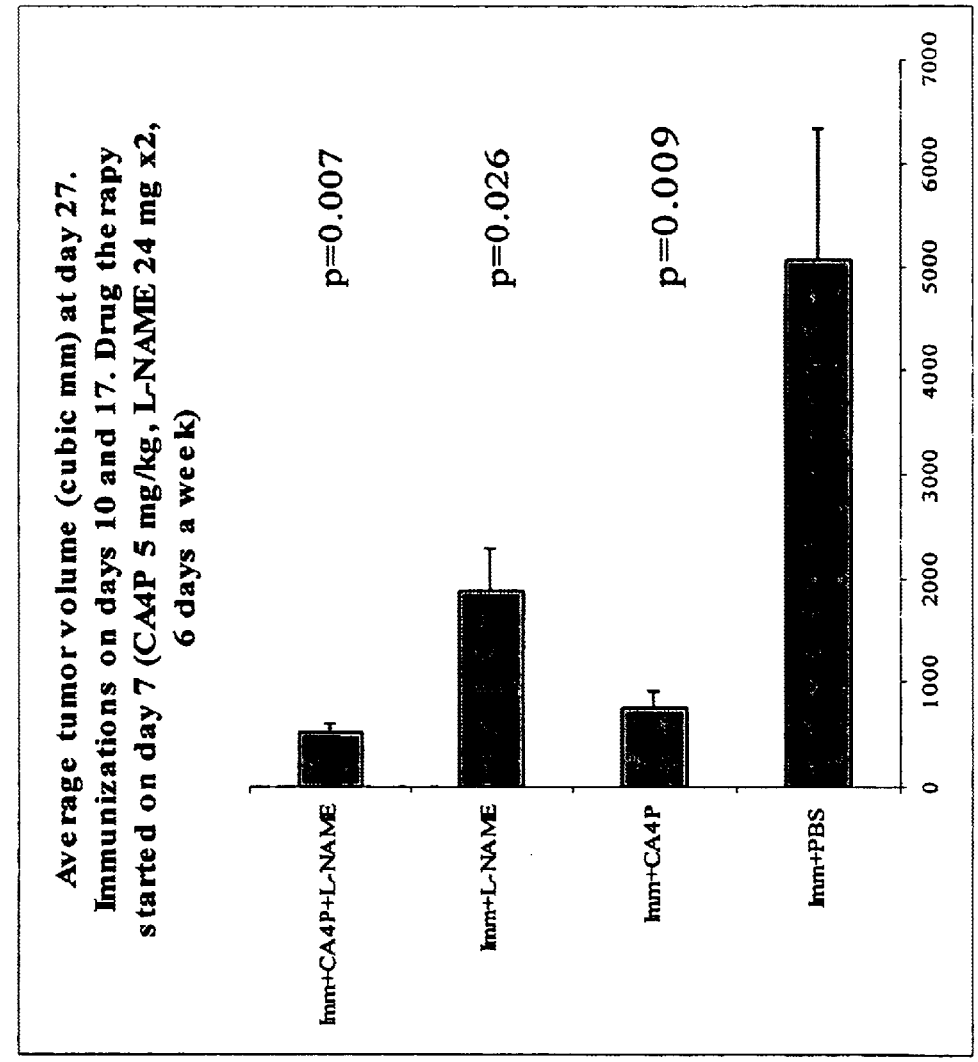
FIG. 6 illustrates enhancement of the therapeutic effect of vaccination with IL-18/IFN-γ producing tumor transfectant 2.0 cells by concurrent treatment with low dose combretastatin-A4 prodrug and/or L-NAME. Mean tumor volume±SEM is indicated. Significance of differences compared to the PBS control was evaluated by the Student's t test. Similarly to L-NAME treatment, CA4P at a dose of 5 mg/kg inhibited the tumor growth significantly compared to the group inoculated with PBS.

Referring to FIG. 6, wild-type (BN7005-H1D2) colon cancer cells were inoculated intrahepatically and combretastatin A4 prodrug treatment began daily on day 7 when the tumors were macroscopically visible. L-NAME, a well known NO inhibitor and effective antitumor agent, was also administered daily. On day 10 and 17 vaccination occurred using BN7005-H1D2 cells transfected with IL-18/IFN-gamma. The data clearly showed that both L-NAME and combretastatin A4 prodrug were effective enhancers of immune stimulated gene therapy. In this case there was only a small enhancement of combining L-NAME with combretastatin A4 prodrug. One likely explanation was that both L-NAME and Combretastatin A4 were doing the same thing; i.e. inhibiting the production of proinflammatory cytokines that cause immune suppression. These data were taken as evidence that in addition to immunotoxic therapy, immune enhancing therapy was also even further enhanced by combretastatin A4 in a similar way that a NO inhibitor did; e.g. by inhibiting the production of immune suppressing proinflammatory cytokines.

EXAMPLE 6

This example provides direct evidence that the observed antitumor growth effects presented in Example 5 were in fact partially relating to stimulating at least some immune cell proliferative responses. For these experiments, wild type H1D2-WT or IL-18 transfected H1D2-IL-18 stimulator cells were used in vitro to test spleen cell proliferative responses in vitro isolated from rats treated in vivo with 2 or 5 mg/kg combretastatin A4 prodrug for 20 days. The cells were cultured in culture and their growth monitored by the incorporation of tritiated thymidine into DNA. First of all, spleenic cells from rats treated with both 2 and 5 mg/kg combretastatin A4 prodrug in vivo showed an enhanced proliferative response for both wild type and IL-18 transfected stimulated cellular responses. These data are highly significant because no vascular toxic effects could be observed in rats treated with 2 mg/kg, hence indicating that any immune modulating effects were independent of targeted effects on tumor microvessels. Secondly, IL-18 transfectant stimulator cells were more effective at enhancing the immune response than wild type cells supporting the interpretation that the response was a true immune modulating effect. Thirdly, the immune modulation was biologically relevant because it was produced under in vivo conditions not an in vitro artifact.

Taken together the data in the Examples clearly demonstrate that selective effects, presumed to be mediated by cytotoxic events which is the case in general with tubulin binding agents, can enhance immunity by reducing production of immune suppressive cytokines. This can be accomplished at doses that do not cause any tumor vascular shut-down, and therefore is another example of previously unknown selective cytotoxic effects induced by combretastatin A4 prodrug and presumably CA4. It is postulated that combretastatin A4 prodrug may be useful in treating immune suppression induced by tumor growth.

It is to be understood that the invention is not limited to the procedures and embodiments hereinabove specifically set forth, but may be carried out in other ways without departure from its spirit.

We claim:

1. A method of counteracting tumor-induced immunosuppression in a warm-blooded animal, comprising administering to the animal an amount of combretastatin A4 or a prodrug thereof, effective to counteract tumor-induced immunosuppression without causing vascular destruction.

2. The method according to claim 1, further comprising administering to the animal a second agent for counteracting tumor-induced immunosuppression.

3. The method according to claim 1, further comprising the administration of immunotherapy to the animal to inhibit or kill tumor cells.

4. The method according to claim 2, wherein said second agent is a selective inhibitor of NOS.

5. A method of counteracting tumor-induced immunosuppression in a warm-blooded animal bearing a tumor comprising subjecting the animal to immunotherapy while administering to the animal an amount of combretastatin A4 or a prodrug thereof, effective to reduce tumor-induced immunosuppression but insufficient to effect destruction of tumor vasculature.

6. The method according to claim 3, wherein said immunotherapy is tumor cell immuno-gene therapy.

7. The method according to claim 6, wherein said immuno-gene therapy comprises vaccinating the animal with tumor cells genetically modified to produce at least one cytokine that augments a cytolytic immune response.

8. A method of modulating anti-tumor immune response in a warm-blooded animal bearing a tumor, comprising administering to the animal an amount of combretastatin A4 or a prodrug thereof, effective to enhance immune responsiveness without causing vascular destruction.

9. The method according to claim 8, further comprising administering to the animal a second agent for modulating the anti-tumor immune response.

10. The method according to claim 8, further comprising the administration of immunotherapy to the animal to inhibit or kill tumor cells.

11. The method according to claim 9, wherein said second agent is a selective inhibitor of NOS.

12. The method according to claim 10, wherein said immunotherapy is tumor cell immuno-gene therapy.

13. The method according to claim 12, wherein said immuno-gene therapy comprises vaccinating the animal with tumor cells genetically modified to produce at least one cytokine that augments a cytolytic immune response.

* * * * *